United States Patent [19]

McRae

[11] Plant 4,179

[45] Jan. 3, 1978

[54] LILLY PLANT: LILIUM 'TWILIGHT'

[75] Inventor: Edward A. McRae, Boring, Oreg.

[73] Assignee: Melridge, Inc., Gresham, Oreg.

[21] Appl. No.: 761,231

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium size flowers of excellent form, strong color, and long persistence, both on the plant and as cut flowers. The flowers of the new plant are particularly characterized by their rose-orchid color tone which is completely new in the upright and outfacing Asiatic divisions of lilies. The plant is highly resistant to disease and shows high tolerance to virus. It is an excellent garden plant. The bulbs may be precooled and forced for cut flowers. The clone is very vigorous and is a good grower and propagator.

1 Drawing Figure

BACKGROUND OF THE INVENTION

My new variety of lily plant originated as a seedling selected from a group of seedlings at Gresham, Oreg. The seedlings were planted as a result of breeding efforts carried on by me since the year 1965. The breeding efforts had as their objective the production of upright and side-facing Asiatic lilies in the rose-orchid color tone, heretofore unknown in the lily breeding art.

I achieved the desired objective by using as the seed parent a clone selected from the complex hybrid strain, Lilium 'Hallmark'. The pollen parent was produced by pollinating an unspotted clone of *Lilium dauricum,* with the pollen of a different clone from the complex hybrid Lilium 'Hallmark' strain.

The flowers of my new lily plant are characterized by a splendid rose-orchid tone. In addition, it possesses to a high degree desirable characteristics of hybrid vigor, great hardiness, and a high degree of disease resistance. It possesses all of the desired characteristics of excellence of form, color and habit. Blooms of medium size are produced on a single stalk. The clone is vigorous and a good grower and propagator, as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the open bloom in full color and illustrates the flower form, the petal arrangement, the connection of the flower to the stalk and in particular the novel and distinctive rose-orchid color tone of the flower.

DESCRIPTION OF THE NEW VARIETY

The following is a detailed description of my new variety of Asiatic hybrid lily, with nomenclature according to *The International Lily Register* (Royal Horticultural Society, London 2nd edition, 1969), and with color designations according to the Royal Society Color Chart, published by the Royal Horticultural Society in 1966.

THE PLANT

Origin: Seedling.

Parentage:

*Seed parent.*—Lilium X 'Hallmark' clone (unpatented).

*Pollen parent.*—Spotless form of *Lilium dauricum X* Lilium cultivar 'Hallmark' clone (unpatented).

Classification:

*Botanic.*—Hybrid Lilium cultivar; Division I-B of Horticultural Classification of Lilies, Royal Horticultural Society.

*Commercial.*—Asiatic hybrid lily.

Form: Single stem erect and stately.

Height: 24 to 30 inches from bulbs 5 to 7 inches in circumference.

Growth: Vigorous and upright.

Foliage:

*Quantity.*—Abundant.

*Size of leaf.*—3 to 4 inches long.

*Shape of leaf.*—Lanceolate.

*Texture.*—Leathery and glossy.

*Color.*—Upper and under sides, both dark green. Foliage becomes purple late in season.

Bulbs:

*Size.*—Any size, ranging to 10 inches in circumference.

*Color.*—White

THE BUD

Form: Obtuse, ovoid and long.

Size: 3 inches long and 1 to 2 inches in circumference increasing as bud develops.

Opening: Bud opens slowly.

Color: Rose pink when outer tepals first divide and also when tepals begin to unfurl.

Tepals: Semi-recurving; rose orchid on the inside and rose orchid with green shading on the outside.

Peduncle: 3 to 4 inches long. Erect to horizontal. Dark green with reddish tinge in color.

THE FLOWER

Blooming habit: Annually in mid-season. Blooms once and profusely.
Size: Medium; about 6 inches in diameter.
Borne: In clusters, as many as 12 on a single stem.
Shape: Flat. Tepals reflex back as bloom matures.
Tepalage:
*Number of Tepals.*—6.
*Arrangement.*—Imbricated.
*Color.*—Rose-orchid at base; rose-orchid R.H.S. C.C.39B at midribs; lighter rose-orchid R.H.S. C.C.38A along the tepal margins; medium pink with green shading on back side.
*Tepal longevity.*—tepals stay on stem about 3 weeks.
*Spotting.*—Moderately spotted in center portion of inner tepals; lightly spotted in center half only of outer tepals; the spots having diameters of from 0.5 to 1.5 m.m.
Pedicel:
*Length.*—3 to 6 inches.
*Color.*—A deepest green with purple shading.
*Form.*—Pedicel is sturdy and upright.
Color change: Flower color intensifies with age after full bloom.
Appearance; The flower is shiny.
Disease resistance: The flower and plant are resistant to disease; in particular, they are resistant to Fusarium and Botrytis.
Fragrance: The flower is not fragrant.
Lasting quality: The flower is long lasting both on the plant and as a cut flower.

THE REPRODUCTIVE ORGANS

Stamens, anthers:
*Arrangement.*—typical of Liliaceae.
*Length.*—2 inches.
*Number.*—6.
*Filaments.*—Length, 2 inches; color, soft cream; green at base.
Pollen and Anthers: Chocolate brown in color.
Pistils: One in number with a length of about 2 inches.
Stigma: Soft purple in color.
Characteristics of ovaries: Typical of genus Lilium.

FRUIT

Fertility: The fruit is fertile.
Shape: The fruit is ovoid in shape.
Color at maturity: The fruit is soft brown.

By reason of its rose-orchid color tone, my new variety of Asiatic hybrid lily is unique and does not resemble any other lily in its class.

I claim:

1. A new and distinctive variety of Asiatic hybrid lily plant substantially as herein shown and described, characterized by its high resistance to disease; its high tolerance to virus; the vigorous growth and propagation characteristics of its clone; the excellence of its flower form; its versatility both as a garden plant and a plant produced from precooled bulbs forced for cut flower; and in particular by its rose-orchid color tone, which is unique in the hybrid Asiatic division of lilies suited to forcing and mass commercial cultivation.

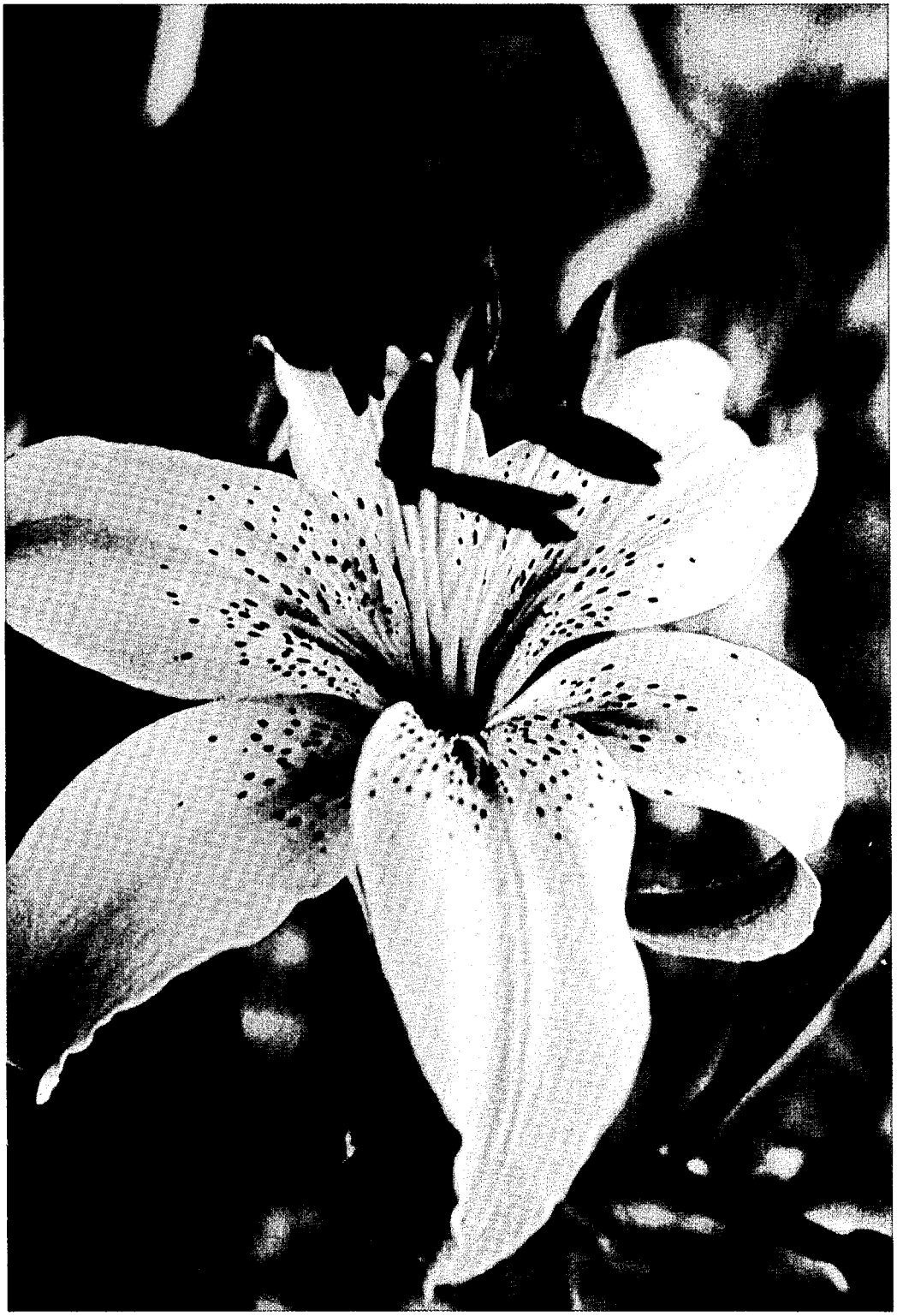

* * * * *